United States Patent [19]

Deflandre et al.

[11] Patent Number: 5,576,354
[45] Date of Patent: Nov. 19, 1996

[54] PHOTOSTABLE COSMETIC SCREENING COMPOSITION CONTAINING A UV-A SCREENING AGENT AND AN ALKYL β,β-DIPHENYLACRYLATE OR α-CYANO-β,β-DIPHENYLACRYLATE

[75] Inventors: André Deflandre, Orry-la-Ville; Michel DuBois, Coulommiers; Serge Forestier, Claye-Scuilly; Hervé Richard, Paris, all of France

[73] Assignee: L'Oreal, Paris, France

[21] Appl. No.: 463,516

[22] Filed: Jun. 5, 1995

Related U.S. Application Data

[62] Division of Ser. No. 937,886, filed as PCT/FR91/00112 Feb. 13, 1991 published as WO91/11989 Aug. 22, 1991, abandoned.

[30] Foreign Application Priority Data

Feb. 14, 1990 [FR] France .................................. 90 01761

[51] Int. Cl.$^6$ ............................ A61K 31/12; A61K 7/42; A61K 7/40
[52] U.S. Cl. ............................ 514/685; 424/59; 558/400; 560/57; 560/101; 568/304
[58] Field of Search ............................ 424/59; 514/685; 558/400; 560/57, 101; 568/304

[56] References Cited

U.S. PATENT DOCUMENTS

| | | | |
|---|---|---|---|
| 3,275,520 | 9/1966 | Strobel et al. | 424/59 |
| 3,393,383 | 7/1968 | Chiron et al. | 333/24.1 |
| 3,961,051 | 6/1976 | Emodi | 424/174 |
| 4,387,089 | 6/1983 | De Polo | 424/59 |
| 4,489,057 | 12/1984 | Welters et al. | 424/47 |
| 4,562,067 | 12/1985 | Hopp et al. | 424/59 |
| 4,568,771 | 2/1986 | Ishihara et al. | 568/421 |
| 4,804,531 | 2/1989 | Grollier | 424/59 |
| 4,810,489 | 3/1989 | Murray | 514/937 |
| 4,837,010 | 6/1989 | Hotta et al. | 424/59 |
| 4,894,222 | 1/1990 | Matravers | 424/59 |

FOREIGN PATENT DOCUMENTS

| | | |
|---|---|---|
| 565859 | 6/1984 | Australia . |
| 718428 | 9/1965 | Canada . |
| 0114607 | 1/1984 | European Pat. Off. . |
| 0255157 | 2/1988 | European Pat. Off. . |
| 1368808 | 6/1964 | France . |
| 2326405 | 10/1976 | France . |
| 2440933 | 6/1980 | France . |
| 2198944 | 6/1988 | United Kingdom . |

OTHER PUBLICATIONS

Encyclopedia of Ultraviolet Absorbers for Sun Products, Cosmetics & Toiletries, vol. 98, Mar. 1983, pp. 43–46.

Shaath, N., "Encyclopedia of UV Absorbers for Sunscreen Products", Cosmetics & Toiletries, vol. 102, Mar. 1987, pp. 21–36.

Thune, P., "Contact and Photocontact Allergy to Sunscreens", Photodermatol., Denmark, Feb. 1984, 1 (1), pp. 5–9 [abstract].

Mathias, C. G., et al, "Allergic Contact Photodermatitis to Para–Aminobenzoic Acid", Arch. Dermatol., Nov. 1978, 114 (11), pp. 1665–1666 [Abstract].

Roelandts, R., et al., "A Survey of Ultraviolet Absorbers in Commercially Available Sun Products", International Journal of Dermatology, May 1983, vol. 22, pp. 247–255.

*Primary Examiner*—Shelley A. Dodson
*Attorney, Agent, or Firm*—Jacobson, Price, Holman & Stern, PLLC

[57] ABSTRACT

A photostable cosmetic screening composition and process for protection of the human epidermis against UV rays of wavelengths between 280 and 380 nm, the composition having, in a cosmetically acceptable vehicle containing at least one fatty phase, 1 to 5% by weight of a dibenzoylmethane derivative and at least 1% by weight of an alkyl β-β-diphenylacrylate or α-cyano-β-β-diphenylacrylate of formula (I), the mole ratio of the compound of formula (I) to the dibenzoylmethane derivative being not less than 0.8.

27 Claims, No Drawings

PHOTOSTABLE COSMETIC SCREENING COMPOSITION CONTAINING A UV-A SCREENING AGENT AND AN ALKYL β,β-DIPHENYLACRYLATE OR α-CYANO-β,β-DIPHENYLACRYLATE

This is a division of application Ser. No. 07/937,886, filed as PCT/FR91/00112 Feb. 13, 1991 published as WO91/11989, now abandoned.

The present invention relates to a photostable cosmetic composition intended for protecting the skin against-UV radiation, containing in combination a UV-A screening agent and an alkyl β,β-diphenylacrylate or α-cyano-β,β-diphenylacrylate, to its use for the protection of the skin against UV rays and to a process for stabilising the UV-A screening agent with an alkyl β,β-diphenylacrylate or α-cyano-β,β-diphenylacrylate.

It is known that light radiation of wavelengths between 280 nm and 400 nm permits tanning of the human epidermis, and that rays of wavelengths between 280 and 320 nm, known by the name of UV-B, cause erythema and burning of the skin which can impair the development of the tan; this UV-B radiation must hence be screened out.

It is also known that UV-A rays, of wavelengths between 320 and 400 nm, causing tanning of the skin, are liable to induce adverse changes in the latter, in particular in the case of sensitive skin or skin continually exposed to solar radiation. UV-A rays cause, in particular, a loss of elasticity of the skin and the appearance of wrinkles, leading to premature ageing. They promote a triggering of the erythematous reaction or enhance this reaction in some subjects, and can even be the source of phototoxic or photoallergic reactions. It is hence also desirable to screen out UV-A radiation.

French Patents No. 2,326,405 and No. 2,440,933 and European Patent No. 114,607 describe dibenzoylmethane derivatives as UV-A screening agents. It is proposed in these patents to combine these UV-A screening agents with various UV-B screening agents with the object of absorbing all the UV radiation of wavelengths between 280 and 380 nm.

Unfortunately, when they are used in combination with these UV-B screening agents, the dibenzoylmethane derivatives described in the abovementioned patents do not always possess sufficient photochemical stability to ensure constant protection during a prolonged exposure to the sun, which necessitates repeated applications at regular and frequent intervals if it is desired to obtain an effective protection of the skin against UV rays.

The Applicant has discovered that, by combining the abovementioned dibenzoylmethane derivatives with an alkyl β,β-diphenytacrylate or α-cyano-β,β-diphenylacrylate of formula

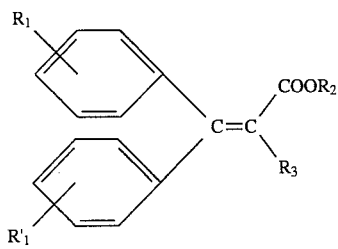

(I)

in well-defined proportions and in a well-defined mole ratio, an exceptional photochemical stability of the dibenzoylmethane derivatives was surprisingly obtained. In addition, such a combination imparts to the screening composition containing it a large sun protection factor as well as good persistence; persistence may be defined as a small change in the protection factor after the subject who has received an application of the screening composition has bathed.

In the general formula (I), the substituents $R_1$ to $R_3$ can assume the following meanings:

$R_1$ and $R'_1$, which may be identical or different, represent a hydrogen atom, a straight- or branched-chain $C_1$–$C_8$ alkoxy radical or a straight- or branched-chain $C_1$–$C_4$ alkyl radical, $R_1$ and $R'_1$ being in the para or meta position;

$R_2$ represents a straight- or branched-chain $C_1$–$C_{12}$ alkyl radical; and $R_3$ represents a hydrogen atom or a CN radical.

Among straight- or branched-chain $C_1$–$C_8$ alkoxy radicals, there may be mentioned, for example, methoxy, ethoxy, n-propoxy, isopropoxy, n-butoxy, isobutoxy, tert-butoxy, n-amyloxy, isoamyloxy, neopentyloxy, n-hexyloxy, n-heptyloxy, n-octyloxy and 2-ethylhexyloxy radicals.

Among straight- or branched-chain $C_1$–$C_4$-alkyl radicals, there may be mentioned, more especially, methyl, ethyl, n-propyl, isopropyl, n-butyl, isobutyl and tert-butyl radicals. For $C_1$–$C_{12}$ alkyl radicals, there may be mentioned, by way of example, in addition to those mentioned above, n-amyl, isoamyl, neopentyl, n-hexyl, n-heptyl, n-octyl, 2-ethylhexyl, decyl and lauryl radicals.

Among the compounds of general formula (I), the following compounds are more especially preferred:

1—2-ethylhexyl α-cyano-β,β-diphenylacrylate,

2—ethyl α-cyano-β,β-diphenylacrylate,

3—2-ethylhexyl-β,β-diphenylacrylate,

4—ethyl β,β-bis(4-methoxyphenyl)acrylate.

Among the dibenzoylmethane derivatives mentioned in the above patents, there may be mentioned especially:

2-methyldibenzoylmethane 4-methyldibenzoylmethane 4-isopropyldibenzoylmethane 4-tert-butyldibenzoylmethane 2,4-dimethyldibenzoylmethane 2,5-dimethyldibenzoylmethane 4,4'-diisopropyldibenzoylmethane 4-tert-butyl-4'-methoxydibenzoylmethane 2-methyl-5-isopropyl-4'-methoxydibenzoylmethane 2-methyl-5-tert-butyl-4'-methoxydibenzoylmethane 2,4-dimethyl-4'-methoxydibenzoylmethane 2,6-dimethyl-4-tert-butyl-4'-methoxydibenzoylmethane.

Among the dibenzoylmethane derivatives mentioned above, special preference is given to 4-tert-butyl-4'-methoxydibenzoylmethane, sold by the company GIVAUDAN under the name "PARSOL 1789", and 4-isopropyldibenzoylmethane, sold by the company MERCK under the name "EUSOLEX 8020".

The derivatives of formula (I) in which $R_3$=CN, $R_1$, $R'_1$ and $R_2$ having the meanings stated above, may be prepared according to the process described in U.S. Pat. No. 3,215,724.

The derivatives of formula (I) in which $R_3$=H, $R_1$, $R'_1$ and $R_2$ having the meanings stated above, may be prepared according to the process described by L. H. KLEMM et al. in J. Org. Chem., 23 (1958) page 344. This process enables the ethyl esters ($R_2$=$C_2H_5$) to be prepared. To prepare the other esters ($R_2 \neq C_2H_5$), the transesterification of the ethyl ester with an alcohol $R_2OH$ ($R_2$ having the meaning stated above except for ethyl) is performed in the presence of para-toluenesulphonic acid.

By virtue of their lipophilic character, the screening agents used distribute uniformly in conventional cosmetic vehicles containing at least one fatty phase, and can thus be applied on the skin to form an effective protective film.

The subject of the present invention is hence a photostable cosmetic composition protecting the skin against UV radiation of wavelengths between 280 and 380 nm, comprising, in a cosmetically acceptable vehicle containing at least one fatty phase, 1 to 5% by weight of dibenzoylmethane derivative and at least 1% by weight of compound of formula (I), the mole ratio of the compound of formula (I) to the dibenzoylmethane derivative being not less than 0.8, and preferably not less than 1.2.

For reasons of solubilisation of the compounds in the composition, this ratio is preferably not more than 8, but this upper limit is not critical.

The subject of the present invention is also a process for protecting the human epidermis against UV rays of wavelengths between 280 and 380 nm, consisting in applying to the skin an effective quantity of a cosmetic composition as defined above.

Another subject of the present invention consists of a process for stabilising dibenzoylmethane derivatives with respect to UV radiation by means of a compound of formula (I), in which process at least 1% by weight of compound of formula (I) is used to stabilise 1 to 5% by weight of dibenzoylmethane derivative, the mole ratio of the compound of formula (I) to the dibenzoylmethane derivative being not less than 0.8.

On account of the lipophilic character of the compounds of formula (I) and dibenzoylmethane derivatives, the cosmetic compositions according to the invention contain at least one fatty phase. They can take the form of oily or oleoalcoholic lotions or the form of fatty or oleoalcoholic gels, of solid sticks, of emulsions such as a cream or milk or of vesicular dispersions of ionic or nonionic amphiphilic lipids; they can be packaged as an aerosol.

As a solubilisation solvent, an oil or wax, lower polyol or monohydric alcohol or mixtures thereof may be used. Especially preferred monohydric alcohols or polyols are ethanol, isopropanol, propylene glycol and glycerol.

The cosmetic composition according to the invention, intended for protecting the human epidermis against ultraviolet rays, can contain the cosmetic adjuvants usual in this type of composition, such as thickeners, emollients, humectants, surfactants, preservatives, antifoams, oils, waxes, lanolin, fragrances, propellants, colourings and/or pigments whose function is to colour the composition itself or the skin, or any other ingredient customarily used in cosmetics.

In addition to the compound of formula (I) and the dibenzoylmethane derivative, the composition can contain other lipophilic UV screening agents.

Art embodiment of the invention is an emulsion in the form of a cream or milk comprising, in addition to the compound of formula (I) combined with the dibenzoylmethane derivative, fatty alcohols, fatty acid esters, and in particular fatty acid triglycerides, fatty acids, lanolin, natural or synthetic oils or waxes and emulsifiers, in the presence of water.

Another embodiment consists of oily lotions based on fatty acid esters, oils and/or natural or synthetic waxes, or of oleoalcoholic lotions based on oils, waxes or fatty acid esters such as fatty acid triglycerides and on lower alcohols such as ethanol or glycols such as propylene glycol and/or polyols such as glycerol.

The oleoalcoholic gels comprise an oil or wax, a lower polyol or alcohol such as ethanol, propylene glycol or glycerol and a thickener such as silica.

The solid sticks consist of fats such as natural or synthetic waxes and oils, fatty alcohols, fatty acid esters and lanolin.

In the case of a composition packaged as an aerosol, conventional propellants such as alkanes, fluoroalkanes and chlorofluoroalkanes are used.

When the composition takes the form of an emulsion or vesicular dispersion, the aqueous phase can contain water-soluble UV screening agents such as benzene-1,4-bis(3-methylidene-10-camphorsulphonic acid) [sic], 2-phenylbenzimidazole-5-sulphonic acid or 2-hydroxy-4-methoxybenzophenone-5-sulphonic acid (UVINUL MS 40), these acids being salified or otherwise.

The examples which follow are intended as illustrations of the invention, no limitation of the latter being, however, implied.

EXAMPLE 1

Nonionic Emulsion

| | |
|---|---|
| 2-Ethylhexyl α-cyano-β,β-diphenylacrylate (UVINUL N 539) | 7.5 g |
| 4-tert-Butyl-4'-methoxydibenzoylmethane (PARSOL 1789) | 1.5 g |
| Mixture of cetyl/stearyl alcohol and cetyl/stearyl alcohol oxyethylenated with 33 moles of ethylene oxide | 7.0 g |
| Mixture of glyceryl mono-, di- and tristearates | 2.0 g |
| Triglycerides of $C_8$–$C_{12}$ fatty acids (Miglyol 812) | 30.0 g |
| Polydimethylsiloxane | 1.5 g |
| Cetyl alcohol | 1.5 g |
| Distilled water q.s. | 100 g |

This emulsion is prepared according to conventional techniques, by dissolving the screening agents in the fatty phase containing the emulsifiers, heating this fatty phase to about 80°–85° C. and adding with brisk stirring the water heated beforehand to about 80° C.

EXAMPLE 2

Sun Oil

The following ingredients are mixed, heating, where appropriate, to 40°–45° C. in order to homogenise:

| | |
|---|---|
| 2-Ethylhexyl β,β-diphenylacrylate | 6.0 g |
| 4-tert-Butyl-4'-methoxydibenzoylmethane (PARSOL 1789) | 3.0 g |
| Isopropyl myristate q.s. | 91.0 g |

EXAMPLE 3

Sun Oil

The following sun oil is prepared in the same manner as in Example 2:

| | |
|---|---|
| Ethyl β,β-bis(4-methoxyphenyl)acrylate | 6.0 g |
| 4-tert-Butyl-4'-methoxydibenzoylmethane (PARSOL 1789) | 3.0 g |
| Isopropyl myristate q.s. | 91.0 g |

EXAMPLE 4

Nonionic Emulsion

| | |
|---|---|
| 2-Ethylhexyl β,β-diphenylacrylate | 6.0 g |
| 4-tert-Butyl-4'-methoxydibenzoylmethane | 1.5 g |
| Mixture of cetyl/stearyl alcohol and cetyl/ stearyl alcohol oxyethylenated with 33 moles of ethylene oxide | 7.0 g |
| Mixture of glyceryl mono-, di- and tristeareates | 2.0 g |
| Triglycerides of $C_8$–$C_{12}$ fatty acids (Miglyol 812) | 30.0 g |
| Polydimethylsiloxane | 1.5 g |
| Cetyl alcohol | 1.5 g |
| Distilled water    q.s. | 100 g |

This emulsion is prepared as in Example 1.

EXAMPLE 5

Water-in-oil Nonionic Emulsion

| | |
|---|---|
| Ethyl β,β-bis(4-methoxyphenyl)acrylate | 3.0 g |
| 4-tert-Butyl-4'-methoxydibenzoylmethane | 2.0 g |
| Mixture of cetyl/stearyl alcohol and cetyl/ stearyl alcohol oxyethylenated with 33 moles of ethylene oxide | 7.0 g |
| Mixture of glyceryl mono-, di- and tristearates | 2.0 g |
| Triglycerides of $C_8$–$C_{12}$ fatty acids (Mygliol [sic] 812) | 30.0 g |
| Polydimethylsiloxane | 1.5 g |
| Cetyl alcohol | 1.5 g |
| Distilled water    q.s. | 100 g |

This emulsion is prepared as in Example 1.

EXAMPLE 6

Oil-in-water Emulsion

| | |
|---|---|
| 2-Ethylhexyl α-cyano-β,β-diphenylacrylate (UVINUL N 539) | 5.0 g |
| 4-Isopropyldibenzoylmethane (EUSOLEX 8020) | 3.0 g |
| Mixture of cetyl/stearyl alcohol and cetyl/ stearyl alcohol oxyethylenated with 33 moles of ethylene oxide, sold by the company HENKEL under the name "SINNOWAX AO" | 7.0 g |
| Non-self-emulsifying mixture of glyceryl mono- and distearates | 2.0 g |
| Cetyl alcohol | 1.5 g |
| Silicone oil | 1.5 g |
| Liquid paraffin | 16.0 g |
| Glycerol | 20.0 g |
| Fragrance, preservative    q.s. | |
| Water    q.s. | 100 g |

The emulsion is produced by adding the fatty phase containing the screening agents and the emulsifiers at approximately 80° C. to the aqueous phase brought to the same temperature and with rapid stirring.

EXAMPLE 7

Oil-in-water Emulsion

| | |
|---|---|
| Ethyl α-cyano-β,β-diphenylacrylate (UVINUL N 35) | 2.0 g |
| 4-tert-Butyl-4'-methoxydibenzoylmethane (PARSOL 1789) | 1.0 g |
| Mixture of cetyl/stearyl alcohol and cetyl/ stearyl alcohol oxyethylenated with 33 moles of ethylene oxide, sold by the company HENKEL under the name "SINNOWAX AO" | 7.0 g |
| Non-self-emulsifying mixture of glyceryl mono- and distearates | 2.0 g |
| Cetyl alcohol | 1.5 g |
| Silicone oil | 1.5 g |
| Liquid paraffin | 20.0 g |
| Glycerol | 20.0 g |
| Fragrance, preservative    q.s. | |
| Water    q.s. | 100 g |

This emulsion is prepared as in Example 6.

EXAMPLE 8

Oil-in-water Emulsion

| | |
|---|---|
| 2-Ethylhexyl α-cyano-β,β-diphenylacrylate (UVINUL N 539) | 8.0 g |
| 4-tert-Butyl-4'-methoxydibenzoylmethane (PARSOL 1789) | 1.0 g |
| Mixture of cetyl/stearyl alcohol and cetyl/ stearyl alcohol oxyethylenated with 33 moles of ethylene oxide, sold by the company HENKEL under the name "SINNOWAX AO" | 7.0 g |
| Non-self-emulsifying mixture of glyceryl mono- and distearates | 2.0 g |
| Cetyl alcohol | 1.5 g |
| Silicone oil | 1.5 g |
| Liquid paraffin | 15.0 g |
| Benzene-1,4-bis(3-methylidene-10-camphor-sulphonic acid)[sic] | 1.0 g AS |
| Glycerol | 20.0 g |
| Fragrance, preservative    q.s. | |
| Water    q.s. | 100 g |

This emulsion is prepared as in Example 6, the water-soluble screening agent being dissolved in the aqueous phase.

We claim:

1. Process for stabilizing dibenzoylmethane derivatives with respect to UV radiation of wavelengths between 280 and 380 nm, comprising adding at least 1% by weight of an alkyl β,β-diphenylacrylate or a α-cyano-β,β-diphenylacrylate of formula:

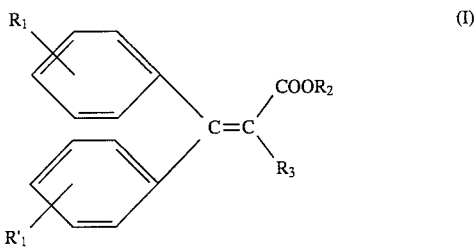

in which
R$_1$ and R'$_1$, which may be identical or different, represent a hydrogen atom, a straight- or branched-chain $C_1$–$C_8$ alkoxy radical or a straight- or branched-chain $C_1$–$C_4$ alkyl radical, R$_1$ and R'$_1$ being in the para or meta position; R$_2$ represents a straight- or branched-chain $C_1$–$C_{12}$ alkyl radical; and $R_3$ represents a hydrogen atom or a —CN radical; to a cosmetic screening composition containing a cosmetically acceptable vehicle having at least one fatty phase and 1 to 5% by weight of a dibenzoylmethane derivative, the mole ratio of the compound of formula (I) to the dibenzoylmethane derivative being not less than 0.8.

2. Process according to claim 1, wherein the mole ratio of the compound of formula (I) to the dibenzoylmethane derivative is not more than 8.

3. Process according to claim 1, wherein the mole ratio of the compound of formula (I) to the dibenzoylmethane derivative is between 1.2 and 8.

4. Process according to claim 1, wherein the dibenzoylmethane derivative is selected from the group consisting of 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, and 2,6-dimethyl-4-tert-butyl-4'-methoxydibenzoylmethane.

5. Process according to claim 1, wherein the dibenzoylmethane derivative is selected from the group consisting of 4-tert-butyl-4'-methoxydibenzoylmethane and 4-isopropyldibenzoylmethane.

6. Process according to claim 1, wherein the compound of formula (I) is selected from the group consisting of 2-ethylhexyl-α-cyano-β,β-diphenylacrylate, ethyl α-cyano-β,β-diphenylacrylate, 2-ethylhexyl β,β-diphenylacrylate and ethyl β,β-bis(4-methoxy-phenyl)acrylate.

7. Process according to claim 1, wherein the cosmetic screening composition is in a form selected from the group consisting of oily and oleoalcoholic lotions, fatty and oleoalcoholic gels, solid sticks, emulsions, a vesicular dispersion of ionic or nonionic amphiphilic lipids, and aerosols.

8. Process according to claim 1, wherein the cosmetic screening composition contains, in addition, at least one cosmetic adjuvant selected from the group consisting of thickeners, emollients, humectants, surfactants, preservatives, antifoaming agents, fragrances, oils, waxes, lower monoalcohols, lower polyols, propellants, colorants and pigments.

9. Process according to claim 1, wherein the cosmetic screening composition constitutes an emulsion in the form of a cream or milk comprising, as a cosmetic vehicle, fatty alcohols, fatty acid esters, and in particular fatty acid triglycerides, fatty acids, lanolin, natural or synthetic oils and waxes and emulsifiers, in the presence of water.

10. Process according to claim 1, wherein the cosmetic screening composition is in the form of an emulsion or a vesicular dispersion, which contains, in addition, water-soluble UV screening agents.

11. Process according to claim 1, wherein the cosmetic screening composition constitutes an oily lotion comprising, as a cosmetic vehicle, fatty acid esters, oils and natural or synthetic waxes.

12. Process according to claim 1, wherein the cosmetic screening composition constitutes an oleoalcoholic lotion comprising, as a cosmetic vehicle, oils, waxes or fatty acid esters, and in particular fatty acid triglycerides, and lower polyols, alcohols and/or glycols.

13. Process according to claim 1, wherein the cosmetic screening composition constitutes an oleoalcoholic gel comprising, as a cosmetic vehicle, a natural or synthetic oil or wax, a lower polyol or alcohol and a thickener.

14. Process for stabilizing dibenzoylmethane derivatives with respect to UV radiation of wavelengths between 280 and 380 nm, consisting essentially of adding at least 1% by weight of an alkyl β,β-diphenylacrylate or a α-cyano-β,β-diphenylacrylate of formula:

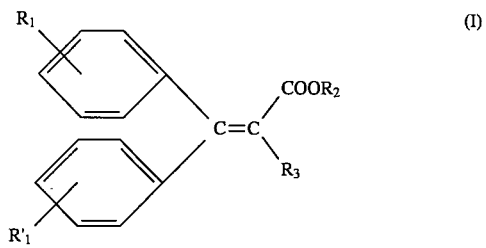

in which $R_1$ and $R'_1$, which may be identical or different represent a hydrogen atom, a straight- or branched-chain $C_1$–$C_8$ alkoxy radical or a straight- or branched-chain $C_1$–$C_4$ alkyl radical, $R_1$ and $R'_1$ being in the para or meta position;

$R_2$ represents a straight- or branched-chain $C_1$–$C_{12}$ alkyl radical; and $R_3$ represents a hydrogen atom or a —CN radical, to a cosmetic screening composition consisting essentially of a cosmetically acceptable vehicle having at least one fatty phase and 1 to 5% by weight of a dibenzoylmethane derivative, the mole ratio of the compound of formula (I) to the dibenzoylmethane derivative being not less than 0.8.

15. In an improved process for stabilizing dibenzoylmethane derivatives with respect to UV radiation of wavelengths between 280 and 380 nm, wherein the improvement consists essentially of addding at least 1% by weight of an alkyl β,β-diphenylacrylate or a α-cyano-β,β-diphenylacrylate of formula:

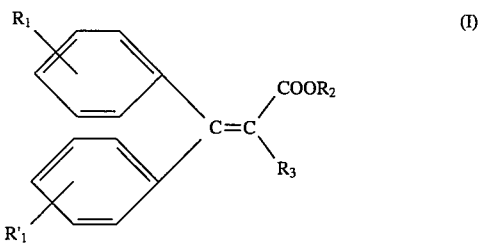

in which $R_1$ and $R'_1$, which may be identical or different, represent a hydrogen atom, a straight- or branched-chain $C_1$–$C_8$ alkoxy radical or a straight- or branched-chain $C_1$–$C_4$ alkyl radical, $R_1$ and $R'_1$ being in the para or meta position;

$R_2$ represents a straight- or branched-chain $C_1$–$C_{12}$ alkyl radical; and $R_3$ represents a hydrogen atom or a —CN radical, to a cosmetic screening composition consisting essentially of a cosmetically acceptable vehicle having at least one fatty phase and 1 to 5% by weight of a dibenzoylmethane derivative, the mole ratio of the compound of formula (I) to the dibenzoylmethane derivative being not less than 0.8.

16. Process for stabilizing dibenzoylmethane derivatives with respect to UV radiation of wavelengths between 280 and 380 nm, comprising adding at least 1% by weight of a α-cyano-β,β-diphenylacrylate of formula:

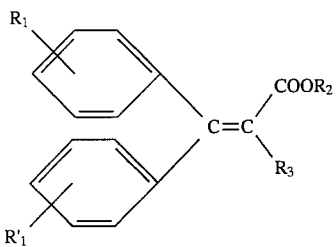

in which
$R_1$ and $R'_1$ represent a hydrogen atom;
$R_2$ represents a 2-ethylhexyl radical; and
$R_3$ represents a —CN radical;
to a cosmetic screening composition comprising a cosmetically acceptable vehicle containing at least one fatty phase and 1 to 5% by weight of a dibenzoylmethane derivative, said dibenzoylmethane derivative being 4-tert-butyl-4'-methoxydibenzoylmethane, the mole ratio of the compound of formula (I) to the dibenzoylmethane derivative being not less than 0.8.

17. Process according to claim 16, wherein the mole ratio of the compound of formula (I) to the dibenzoylmethane derivative is not more than 8.

18. Process according to claim 16, wherein the mole ratio of the compound of formula (I) to the dibenzoylmethane derivative is between 1.2 and 8.

19. Process according to claim 16, wherein the cosmetic screening composition is in a form selected from the group consisting of oily and oleoalcoholic lotions, fatty and oleoalcoholic gels, solid sticks, emulsions, a vesicular dispersion of ionic or nonionic amphiphilic lipids, and aerosols.

20. Process according to claim 16, wherein the cosmetic screening composition contains, in addition, at least one cosmetic adjuvant selected from the group consisting of thickeners, emollients, humectants, surfactants, preservatives, antifoaming agents, fragrances, oils, waxes, lower monoalcohols, lower polyols, propellents, colorants and pigments.

21. Process according to claim 16, wherein the cosmetic screening composition constitutes an emulsion in the form of a cream or milk comprising, as a cosmetic vehicle, fatty alcohols, fatty acid asters, and in particular fatty acid triglycerides, fatty acids, lanolin, natural or synthetic oils and waxes and emulsifiers, in the presence of water.

22. Process according to claim 16, wherein the cosmetic screening composition is in the form of an emulsion or a vesicular dispersion, which contains, in addition, water-soluble UV screening agents.

23. Process according to claim 16, wherein the cosmetic screening composition constitutes an oily lotion comprising, as a cosmetic vehicle, fatty acid esters, oils and natural or synthetic waxes.

24. Process according to claim 16, wherein the cosmetic screening composition constitutes an oleoalcoholic lotion comprising, as a cosmetic vehicle, oils, waxes or fatty acid esters, and in particular fatty acid triglycerides, and lower polyols, alcohols and/or glycols.

25. Process according to claim 16, wherein the cosmetic screening composition constitutes an oleoalcoholic gel comprising, as a cosmetic vehicle, a natural or synthetic oil or wax, a lower polyol or alcohol and a thickener.

26. Process for stabilizing dibenzoylmethane derivatives with respect to UV radiation of wavelengths between 280 and 380 nm consisting essentially of adding at least 1% by weight of a α-cyano β,β-diphenylacrylate of formula:

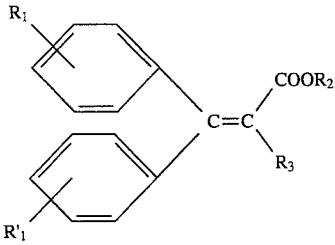

in which
$R_1$ and $R'_1$ represent a hydrogen atom;
$R_2$ represents 2-ethylhexyl radical; and
$R_3$ represents a —CN radical;
to a cosmetic screening composition consisting essentially of a cosmetically acceptable vehicle containing at least one fatty phase and 1 to 5% by weight of a dibenzoylmethane derivative, said dibenzoylmethane derivative being 4-tert-butyl-4'-methoxydibenzoylmethane, the mole ratio of the compound of formula (I) to the dibenzoylmethane derivative being not less than 0.8.

27. In an improved process for stabilizing dibenzoylmethane derivatives with respect to UV radiation of wavelengths between 280 and 380 nm, said dibenzoylmethane derivative being 4-tert-butyl-4'-methoxydibenzoylmethane, wherein the improvement consists essentially of adding at least 1% by weight of a α-cyano-β,β-diphenylacrylate of formula:

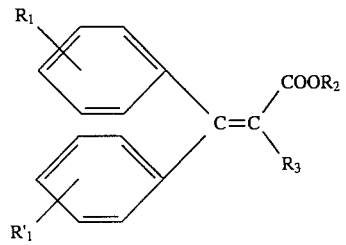

in which
$R_1$ and $R'_1$ represent a hydrogen atom;
$R_2$ represents 2-ethylhexyl radical; and
$R_3$ represents a —CN radical;
to a cosmetic screening composition consisting essentially of a cosmetically acceptable vehicle containing at least one fatty phase and 1 to 5% by weight of 4-tert-butyl-4'-methoxydibenzoylmethane, the mole ratio of the compound of formula (I) to 4-tert-butyl-4'-methoxydibenzoylmethane being not less than 0.8.

* * * * *